(12) United States Patent
Lin et al.

(10) Patent No.: US 7,226,986 B2
(45) Date of Patent: *Jun. 5, 2007

(54) PROCESS FOR PRODUCTION OF A CARBOXYLIC ACID/DIOL MIXTURE SUITABLE FOR USE IN POLYESTER PRODUCTION

(75) Inventors: Robert Lin, Kingsport, TN (US); Timothy Alan Upshaw, Kingsport, TN (US); Duane Alan Hall, Lexington, SC (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/077,481

(22) Filed: Mar. 10, 2005

(65) Prior Publication Data
US 2005/0228164 A1  Oct. 13, 2005

Related U.S. Application Data

(63) Continuation-in-part of application No. 10/383,126, filed on Mar. 6, 2003.

(51) Int. Cl.
*C08G 63/00* (2006.01)

(52) U.S. Cl. .......... 528/308; 560/80; 562/485

(58) Field of Classification Search ........ 528/308; 560/80; 562/485
See application file for complete search history.

(56) References Cited

U.S. PATENT DOCUMENTS

| | | | |
|---|---|---|---|
| 3,057,909 A | 10/1962 | Sebelist et al. |
| 3,064,044 A | 11/1962 | Baldwin |
| 3,584,039 A | 6/1971 | Meyer |
| 3,683,018 A | 8/1972 | Longland, Jr. |
| 3,839,436 A | 10/1974 | Longland, Jr. |
| 3,850,983 A | 11/1974 | Park |
| 3,931,305 A | 1/1976 | Fisher |
| 4,051,178 A | 9/1977 | Kimura et al. |
| 4,201,871 A | 5/1980 | Tanouchi et al. |
| 4,212,995 A | 7/1980 | Shiraki |
| 4,268,690 A | 5/1981 | Komatsu et al. |
| 4,330,676 A | 5/1982 | Moxham |
| 4,334,086 A | 6/1982 | Hanotier et al. |
| 4,357,475 A | 11/1982 | Hanotier et al. |
| 4,380,662 A | 4/1983 | Hanotier et al. |
| 4,500,732 A | 2/1985 | Petty-Weeks et al. |
| 4,588,414 A | 5/1986 | Takegami et al. |
| 4,707,274 A | 11/1987 | Donhauser et al. |
| 4,782,181 A | 11/1988 | James |
| 4,812,233 A | 3/1989 | Coenen et al. |
| 4,861,919 A | 8/1989 | Robbins et al. |
| 4,892,972 A | 1/1990 | Schroeder et al. |
| 4,939,297 A | 7/1990 | Browder et al. |
| 5,008,450 A | 4/1991 | Yamamoto et al. |
| 5,080,721 A | 1/1992 | Flanigan et al. |
| 5,095,146 A | 3/1992 | Zeitlin et al. |
| 5,107,874 A | 4/1992 | Flanigan et al. |
| 5,116,423 A | 5/1992 | Kokkonen et al. |
| 5,143,554 A | 9/1992 | Koyama et al. |
| 5,175,355 A | 12/1992 | Streich et al. |
| 5,200,557 A | 4/1993 | Gee et al. |
| 5,454,959 A | 10/1995 | Stevens |
| 5,476,919 A | 12/1995 | Schaeffer |
| 5,527,957 A | 6/1996 | Hindmarsh et al. |
| 5,563,293 A | 10/1996 | Hindmarsh et al. |
| 5,567,842 A | 10/1996 | Izumisawa et al. |
| 5,583,254 A | 12/1996 | Turner et al. |
| 5,616,792 A | 4/1997 | Bartos et al. |
| 5,635,074 A | 6/1997 | Stenstrom et al. |
| 5,643,468 A | 7/1997 | Ure |
| 5,653,673 A | 8/1997 | Desai et al. |
| 5,676,847 A | 10/1997 | Yamamoto et al. |
| 5,679,846 A | 10/1997 | Hindmarsh et al. |
| 5,684,187 A | 11/1997 | Ohkoshi et al. |
| 5,698,734 A | 12/1997 | Turner et al. |
| 5,712,412 A | 1/1998 | Inary et al. |
| 5,777,161 A | 7/1998 | Inary |

(Continued)

FOREIGN PATENT DOCUMENTS

CA    1067095    11/1979

(Continued)

OTHER PUBLICATIONS

M. Matias, R. Bacai Oglu, R.F. Paie & H.H. Glatt, "Study of Di- and Polyesterification, I. Esterification of Ethylene and Diethylene Glycols with Acetic Acid", (1978), Chemical Bulletin of the Technical University of Timisoara, 23(37), pp. 73-76.

(Continued)

*Primary Examiner*—Terressa Boykin
(74) *Attorney, Agent, or Firm*—Steven A. Owen; Bernard J. Graves, Jr.

(57) ABSTRACT

The present invention relates to a process by which a carboxylic acid/diol mixture is obtained from a carboxylic acid/solvent slurry without isolation of a substantially dry carboxylic acid solid. More specifically, the present invention relates to a process by which a terephthalic acid/ethylene glycol mixture is obtained from a terephthalic acid/solvent slurry without isolation of a substantially dry terephthalic acid solid.

30 Claims, 1 Drawing Sheet

U.S. PATENT DOCUMENTS

| | | |
|---|---|---|
| 5,840,965 A | 11/1998 | Turner et al. |
| 5,840,968 A | 11/1998 | Lee et al. |
| 5,925,786 A | 7/1999 | Isayama et al. |
| 5,955,394 A | 9/1999 | Kelly |
| 5,971,907 A | 10/1999 | Johannemann et al. |
| 5,973,196 A | 10/1999 | Takano et al. |
| 6,013,835 A | 1/2000 | Lee et al. |
| 6,153,790 A | 11/2000 | June et al. |
| 6,162,837 A | 12/2000 | Gerking et al. |
| 6,228,215 B1 | 5/2001 | Hoffman, Jr. |
| 6,297,348 B1 | 10/2001 | Rodden et al. |
| 6,307,099 B1 | 10/2001 | Turner et al. |
| 6,495,044 B1 | 12/2002 | Verdoes |
| 6,517,733 B1 | 2/2003 | Carlson |
| 6,797,073 B1 | 9/2004 | Teruggi et al. |
| 2003/0004372 A1 | 1/2003 | Piras et al. |
| 2004/0073059 A1 | 4/2004 | Lin |
| 2004/0176635 A1 | 9/2004 | Lin et al. |
| 2004/0245176 A1 | 12/2004 | Parker et al. |
| 2005/0087215 A1 | 4/2005 | Miyahara et al. |
| 2005/0159578 A1 | 7/2005 | Parker et al. |

FOREIGN PATENT DOCUMENTS

| | | |
|---|---|---|
| CN | 1299806 | 6/2001 |
| DE | 31 28 474 | 6/1982 |
| DE | 33 28 543 | 3/1985 |
| EP | 0 370 083 | 6/1994 |
| GB | 994 769 | 6/1965 |
| GB | 1059840 | 2/1967 |
| GB | 1334452 | 10/1973 |
| GB | 1498031 | 1/1978 |
| GB | 1589310 | 5/1981 |
| JP | 48-15848 | 2/1973 |
| JP | 48026740 * | 4/1973 |
| JP | 48-67239 | 9/1973 |
| JP | 52-113940 | 11/1977 |
| JP | 53-53634 | 5/1978 |
| JP | 53-90233 | 8/1978 |
| JP | 53-90234 | 8/1978 |
| JP | 55-33421 | 3/1980 |
| JP | 7-149690 | 6/1995 |
| JP | 7-291896 | 11/1995 |
| JP | 9-255619 | 9/1997 |
| JP | 9-286758 | 11/1997 |
| JP | 9-286759 | 11/1997 |
| JP | 10-36313 | 2/1998 |
| JP | 2003-62405 | 3/2003 |
| JP | 2003-128624 | 5/2003 |
| SU | 1042809 | 1/1971 |
| WO | WO 93/24440 | 12/1993 |
| WO | WO 97/17391 A | 5/1997 |
| WO | WO 98/38150 | 9/1998 |
| WO | WO 98/38150 A1 | 9/1998 |
| WO | WO 99/08990 | 2/1999 |
| WO | WO 03/020680 | 3/2003 |

OTHER PUBLICATIONS

Arun Pal Aneja and Viney Pal Aneja, "The Effect of Water and Air Contamination on Poly (Ethylene Terephthalate) Formation", *Polymer Engineering Reviews*, 1982, pp. 123-133, vol. 2, No. 2.

Allen, Norman S., Edge, Michele, Daniels, James, Royall, David, "*Spectroscopic Analysis of Organic Contaminants in Terphthalic Acid: Colour Implications in Poly(ethylene terephthalate) Manufacture*", Polymer Degradation and Stability, 1998, pp. 373-383, 62, Great Britain.

USPTO Office Action for U.S. Appl. No. 10/271,058 dated Apr. 6, 2004.

USPTO Office Action for U.S. Appl. No. 10/383,126 dated Jun. 28, 2004.

USPTO Notice of Allowability for U.S. Appl. No. 10/758,678 dated Jul. 6, 2004.

USPTO Office Action for U.S. Appl. No. 10/271,058 dated Jul. 15, 2004.

USPTO Office Action for U.S. Appl. No. 10/758,678 dated Dec. 8, 2004.

USPTO Office Action for U.S. Appl. No. 10/383,126 dated Dec. 22, 2004.

USPTO Office Action for U.S. Appl. No. 10/271,058 dated Dec. 22, 2004.

USPTO Office Action for U.S. Appl. No. 10/758,678 dated Jun. 29, 2005.

USPTO Office Action dated Mar. 3, 2006 for U.S. Appl. No. 10/383,126.

USPTO office action dated Aug. 4, 2006 for copending U.S. Appl. No. 10/758,678.

USPTO office action dated Nov. 1, 2006 for copending U.S. Appl. No. 10/271,058.

USPTO Office Action dated Oct. 3, 2004 for U.S. Appl. No. 11/077,481.

* cited by examiner

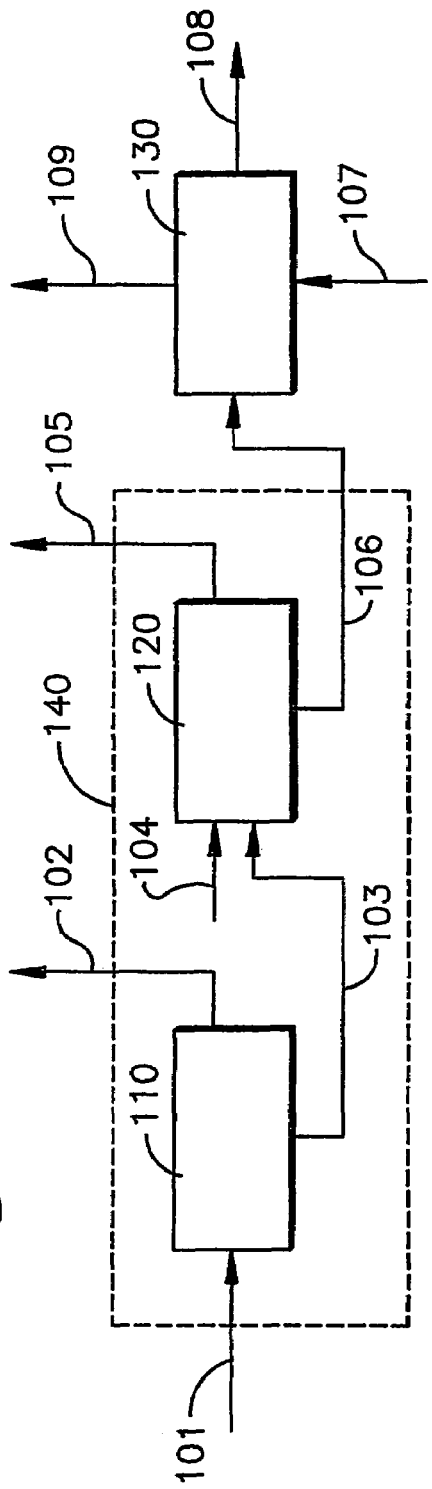
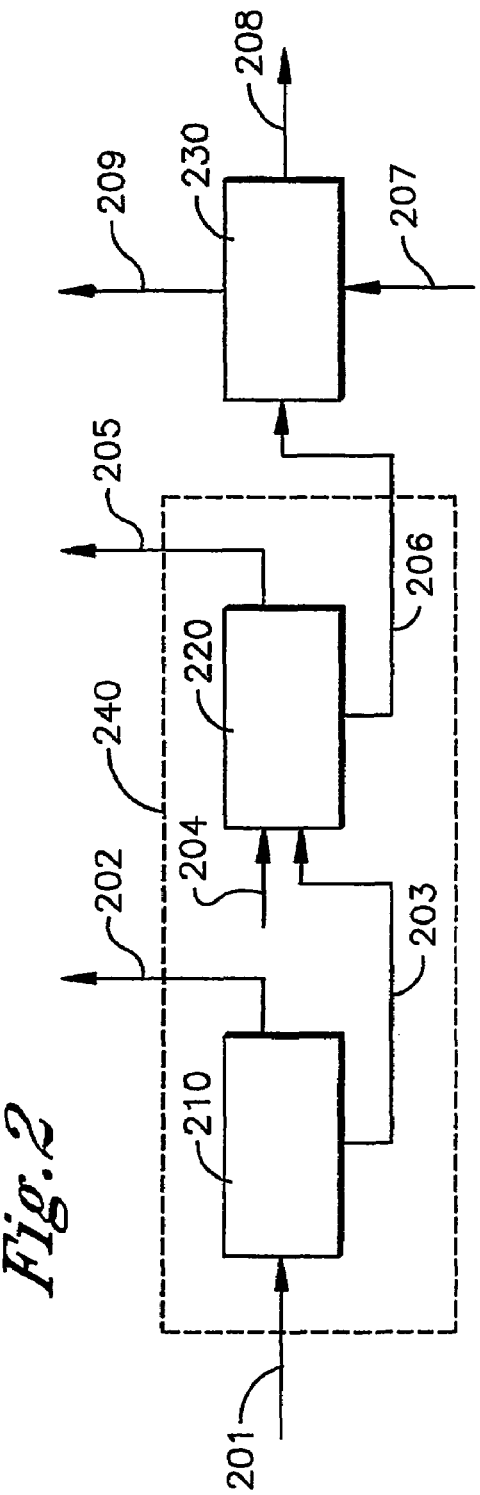

PROCESS FOR PRODUCTION OF A CARBOXYLIC ACID/DIOL MIXTURE SUITABLE FOR USE IN POLYESTER PRODUCTION

CROSS REFERENCE TO RELATED APPLICATION

This application is a continuation-in-part of copending U.S. application Ser. No. 10/383,126, filed Mar. 6, 2003, hereby incorporated by reference in its entirety to the extent that they do not contradict statements herein.

FIELD OF INVENTION

The present invention relates to a process by which a carboxylic acid/diol mixture is obtained from a carboxylic acid/solvent slurry without isolation of a substantially dry carboxylic acid solid. More specifically, the present invention relates to a process by which a terephthalic acid/diol mixture suitable as a starting material for polyester production is obtained from a terephthalic acid/solvent slurry without isolation of a substantially dry terephthalic acid solid.

BACKGROUND OF THE INVENTION

Pursuant to the goal of making polyethylene terephthalate (PET) and other polyesters, a great deal of patent literature is dedicated to the describing processes for preparing a carboxylic acid/diol mixture suitable as starting material. In general, these inventions describe specific mixing schemes with a purified terephthalic acid solid and liquid ethylene glycol. Additionally, there is substantial body of literature devoted to producing a purified terephthalic acid in the powder form that is suitable for use in producing PET and other polyesters.

The objective of this invention is to describe a process by which the carboxylic acid/diol mixture suitable as a starting material for polyester production is obtained from a carboxylic acid/solvent slurry without isolation of a substantially dry carboxylic acid solid. More specifically, the objective of this invention is to describe a process by which a terephthalic acid/diol mixture suitable as a starting material for polyester production is obtained from a terephthalic acid/solvent slurry without isolation of a substantially dry terephthalic acid solid.

Usually, purified terephthalic acid solid is produced in a multi-step process wherein a crude terephthalic acid is produced. The crude terephthalic acid does not have sufficient quality for direct use as starting material in commercial PET. Instead, the crude terephthalic acid is usually refined to purified terephthalic acid solid.

Liquid phase oxidation of p-xylene produces crude terephthalic acid. The crude terephthalic acid is dissolved in water and hydrogenated for the purpose of converting 4-carboxybenzaldehyde to p-toluic acid, which is a more water-soluble derivative, and for the purpose of converting characteristically yellow compounds to colorless derivatives. Any 4-carboxybenzaldehyde and p-toluic acid in the final purified terephthalic acid product is particularly detrimental to polymerization processes as they act as a chain terminator during the condensation reaction between terephthalic acid and ethylene glycol in the production of PET. Typical purified terephthalic acid contains on a weight basis less than 25 parts per million (ppm) 4-carboxybenzaldehyde and less than 150 ppm p-toluic acid.

A number of other processes have been developed where a terephthalic acid suitable as starting material for commercial PET production without the use of hydrogenation. Typically, these processes usually involve catalyzed oxidation of p-xylene in an acetic acid solvent followed by filtration and drying of the terephthalic acid from the acetic acid solvent.

To produce a terephthalic acid/diol mixture acceptable for PET production from a terephthalic acid/solvent slurry poses a substantially different problem than from a terephthalic acid and water mixture.

Typically, TPA produced via catalyzed oxidation of p-xylene in an acetic acid solvent produces a terephthalic acid/solvent slurry that contains residual catalyst (e.g cobalt, manganese, and bromine). In a common method of producing a substantially dry TPA solid from a terephthalic acid/solvent slurry, the terephthalic acid/solvent slurry is filtered to separate a substantial amount of the acetic acid liquid from the TPA solids. Residual catalyst is usually separated from the terephthalic acid/solvent slurry by washing (rinsing) the wet cake with catalyst-free acetic acid, water or other solvent. The TPA solid is isolated by drying.

In the present invention, a novel process has been discovered resulting in fewer steps than the currently employed processes. The primary utility of the invention is reduction of capital and operating costs associated with the isolation of a terephthalic acid powder. In the conventional approach toward producing terephthalic acid via catalyzed oxidation of p-xylene in an acetic acid solvent, a terephthalic acid/solvent slurry is filtered, washed, then dried to produce a terephthalic acid powder suitable as starting material for PET production.

In one embodiment of the present invention, the terephthalic acid/solvent slurry is filtered to produce a terephthalic acid cake with solvent and a TPA solvent mother liquor stream. The terephthalic acid cake with solvent is then washed (rinsed) with water to recover residual metal catalyst material and to produce a water-wet terephthalic acid cake and an TPA solvent/water by-product liquor. The water-wet terephthalic acid cake is then combined with a diol to produce a terephthalic acid/diol mixture suitable as starting material in a commercial PET process. By bypassing conventional processes for isolating a terephthalic acid solid, the equipment necessary produce a terephthalic acid powder is eliminated.

Another surprising and seemingly contradictory aspect of the invention is the benefit of addition of water to the acetic acid and ethylene glycol solvents. In general, in conventional processes for producing terephthalic acid, it is necessary to remove water produced in the oxidation process. Typically, use of acetic acid as an oxidation solvent necessitates an additional process step where acetic acid and water are separated. It is seemingly contradictory to produce an acetic acid and water mixture when it can be avoided by drying the terephthalic acid from the acetic acid solvent.

Additionally, in processes for producing PET via esterification of TPA with ethylene glycol, water is generated as a reaction by-product. In general, it is necessary to remove the water produced in the esterification process via an additional process step where ethylene glycol and water are separated. It is seemingly contradictory to produce an ethylene glycol and water mixture when it can be avoided by not introducing water with the TPA.

However, the one benefit of this invention is based on the premise that ethylene glycol/water and acetic acid/water separation systems normally exist for conventional TPA and PET production processes. In this invention, the savings associated with eliminating the TPA drying is of greater benefit than the incremental increase in ethylene glycol and water separation capacity plus the incremental increase in acetic acid and water separation capacity.

SUMMARY OF THE INVENTION

The present invention relates to a process by which a carboxylic acid/diol mixture is obtained from a carboxylic acid/solvent slurry without isolation of a substantially dry carboxylic acid solid. More specifically, the present invention relates to a process for the production of a terephthalic acid/ethylene glycol mixture suitable as feedstock for the production of commercial PET. The resulting process has fewer steps than currently employed processes and can be constructed at lower capital cost. Specifically, the present invention incorporates a direct displacement of water with ethylene glycol. Incorporation of the displacement step eliminates the need to isolate a purified terephthalic acid solid thereby eliminating the need for crystallization, solid-liquid separation, and solids handling equipment normally found in commercial purified terephthalic acid processes.

It is an object of this invention to provide a process for producing a carboxylic acid/diol mixture from a carboxylic acid/solvent slurry without isolation of a substantially dry carboxylic acid solid.

It is another object of this invention to provide a process for producing a terephthalic acid/diol mixture from a terephthalic acid/solvent slurry without isolation of a substantially dry terephthalic acid solid.

It is another object of this invention to provide a process for producing a terephthalic acid/ethylene glycol mixture from a terephthalic acid solvent slurry without isolation of a substantially dry terephthalic acid solid.

It is another object of this invention to provide a process for producing a terephthalic acid/ethylene glycol mixture without isolation of a substantially dry terephthalic acid solid by removing water from a water-wet terephthalic acid cake through the use of a carboxylic acid/diol mixing zone.

In a first embodiment of this invention, a process for producing a carboxylic acid/diol mixture is provided comprising the adding a diol to a water-wet carboxylic acid cake in a carboxylic acid/diol mixing zone to remove a portion of the water to form the carboxylic acid/diol mixture.

In another embodiment of this invention, a process for producing a carboxylic acid/diol mixture is provided, the process comprising the following steps:

(a) removing in a first solid-liquid separation device impurities from a carboxylic acid/solvent slurry to form a carboxylic acid cake with acetic acid and a solvent mother liquor stream.

(b) removing a portion of a solvent in a second solid-liquid separation device from the carboxylic acid cake with acetic acid to form a water-wet carboxylic acid cake and a solvent/water byproduct liquor.

(c) adding a diol to the water-wet carboxylic acid cake in a carboxylic acid/diol mixing zone to remove a portion of the water to form the carboxylic acid/diol mixture.

In another embodiment of this invention, a process for producing a carboxylic acid/diol mixture is provided, the process comprising the following steps:

(a) removing a solvent from a carboxylic acid/solvent slurry in a solid-liquid separation zone; wherein a portion of the solvent in the carboxylic acid/solvent slurry is replaced with water to form a water-wet carboxylic acid cake.

(b) adding a diol to the water-wet carboxylic acid cake in a carboxylic acid/diol mixing zone to remove a portion of the water to form the carboxylic acid/diol mixture.

In another embodiment of this invention, a process for producing a terephthalic acid/diol mixture is provided, the process comprising the adding a diol to a water-wet terephthalic acid cake in a terephthalic acid/diol mixing zone to remove a portion of the water to form the terephthalic acid/diol mixture.

In another embodiment of this invention, a process for producing a terephthalic acid/diol mixture is provided, the process comprising the following steps:

(a) removing in a first solid-liquid separation device impurities from a terephthalic acid/solvent slurry to for a terephthalic acid cake with acetic acid.

(b) removing a portion of a solvent in a second solid-liquid separation device to form the terephthalic acid cake with acetic acid to form a water-wet terephthalic acid cake.

(c) adding a diol to the water-wet terephthalic acid cake in a terephthalic acid/diol mixing zone to remove a portion of the water to form the terephthalic acid/diol mixture.

In another embodiment of this invention, a process for producing a terephthalic acid/diol mixture is provided, the process comprising the following steps:

(a) removing a solvent from a terephthalic acid/solvent slurry in a solid-liquid separation zone; wherein a portion of the solvent in the terephthalic acid/solvent slurry is replaced with water to form a water-wet terephthalic acid cake.

(b) adding a diol to the water-wet terephthalic acid cake in a terephthalic acid/diol mixing zone to remove a portion of the water to form the terephthalic acid/diol mixture.

In another embodiment of this invention, a process to produce a carboxylic acid/diol mixture from a carboxylic acid/solvent slurry is provided without the isolation of a substantially dry carboxylic acid solid.

In another embodiment of this invention, a process to produce a terephthalic/diol mixture from a terephthalic acid/solvent slurry is provided, without the isolation of a substantially dry terephthalic acid solid.

In another embodiment of this invention a process for producing a terephthalic acid/diol mixture is provided, the process comprising the following steps:

(a) removing in a first solid-liquid separation device impurities from a terephthalic acid/solvent slurry to form a terephthalic acid cake with acetic acid; wherein the first solid-liquid separation device is operated at a temperature between about 40° C. to about 155° C.

(b) removing a portion of a solvent in a second solid-liquid separation device to form the terephthalic acid cake with acetic acid to form a water-wet terephthalic acid cake; wherein the second solid-liquid separation device is operated at a temperature between about 40 C to about 155.

(c) adding a diol to the water-wet terephthalic acid cake in a terephthalic acid/diol mixing zone to remove a portion of the water to form the terephthalic acid/diol mixture; wherein the adding occurs at a temperature between about 40° C. and 290° C.; wherein the diol is ethylene glycol.

In another embodiment of this invention, a process for producing a terephthalic acid/diol mixture is provided, the process comprising the following steps in the order named:

(a) removing in a first solid-liquid separation device impurities from a terephthalic acid/solvent slurry to form a terephthalic acid cake with acetic acid; wherein the first solid-liquid separation device is operated at a temperature between about 40° C. to about 155° C.

(b) removing a portion of a solvent in a second solid-liquid separation device to form the terephthalic acid cake with acetic acid to form a water-wet terephthalic acid cake; wherein the second solid-liquid separation device is operated at a temperature between about 40 C to about 155.

(c) adding a diol to the water-wet terephthalic acid cake in a terephthalic acid/diol mixing zone to remove a portion of the water to form the terephthalic acid/diol mixture; wherein the adding occurs at a temperature between about 40° C. and 290° C.; wherein the diol is ethylene glycol.

These objects, and other objects, will become more apparent to others with ordinary skill in the art after reading this disclosure.

DESCRIPTION OF THE INVENTION

In a first embodiment of this invention shown in FIG. 1, a process for producing a carboxylic acid/diol mixture 108 is provided, the process comprises adding a diol 107 to a water-wet carboxylic acid cake 106 in a carboxylic acid/diol mixing zone 130 to remove a portion of the water to form the carboxylic acid/diol mixture 108.

The carboxylic acid/diol mixing zone 130, the diol 107, the carboxylic acid/diol mixture 108 and the water-wet carboxylic acid cake 106 is described subsequently in a second embodiment of this invention.

In the second embodiment of this invention shown in FIG. 1, a process for producing a carboxylic acid/diol mixture 108 is provided. The process comprises the following steps.

Step (1) comprises removing in a first solid-liquid separation device 110 impurities from a carboxylic acid/solvent slurry 101 to form a carboxylic acid cake with solvent 103 and a solvent mother liquor stream 102. Conduit 101 contains a carboxylic acid/solvent slurry comprising a carboxylic acid, impurities and a solvent. The impurities comprises residual catalyst (typically but not limited to cobalt, manganese, or bromine). Suitable solvents include, but are not limited to, aliphatic mono-carboxylic acids, preferably containing 2 to 6 carbon atoms, or benzoic acid and mixtures thereof and mixtures of these compounds with water. Preferably, the solvent is comprised of mainly acetic acid and/or some water. The ratio of acetic acid to water can range from 50:50 to 99:1 acetic acid to water by mass, more preferably in the range of 85:15 to 95:5, and most preferably in the range of 90:10 to 95:5. Suitable carboxylic acids include by are not limited to terephthalic acid, isophthalic acid, naphthalene dicarboxylic acid, trimellitic acid, and mixtures thereof.

The carboxylic acid/solvent slurry 101 is in the range of 10-40% by weight carboxylic acid. Preferably the carboxylic acid/solvent slurry 101 is in the range of 25-35% by weight carboxylic acid. Most preferably, the carboxylic acid/solvent slurry 101 is in the range of 30-35% by weight carboxylic acid. The carboxylic acid/solvent slurry in conduit 101 is then introduced into a first solid-liquid separation device, 110, wherein a portion of the solvent mother liquor is recovered in conduit 102. The solvent mother liquor 102 comprises a portion of the solvent.

The first solid-liquid separation device 110 comprises any device capable of efficiently separating solids and liquids. The first solid-liquid separation device 110 can typically be comprised of, but not limited to, the following types of devices: centrifuges, cyclones, rotary drum filters, belt filters, press filters, etc. The first solid-liquid separation device 110 can operate within a temperature range of from approximately 40° C. to 155° C. Preferably the first solid-liquid separation device 110 can operate within a temperature range of from approximately 80° C. to 150° C. Most preferably the first solid-liquid separation device 110 can operate within a temperature range of from approximately 90° C. to 150° C. A carboxylic acid cake with solvent 103, is produced wherein the moisture composition of the carboxylic acid cake with solvent 103 is in the range of 0.5-30% by weight moisture, preferably in the range of 1-20% moisture, most preferably in the range of 1-5% moisture. Optionally, the residual solvent can be removed by a gas displacement step to minimize solvent contamination with wash.

Step (2) comprises removing a portion of a solvent in a second solid-liquid separation device 120 from the carboxylic acid cake with solvent 103 to form a water-wet carboxylic acid cake 106 and a solvent/water byproduct liquor 105.

The carboxylic acid cake with solvent 103, is then subjected to a wash or "rinsing" with water or water with residual amounts of solvent in the solid-liquid separation device, 120, wherein a portion of the initial solvent is replaced with water to form a water-wet carboxylic acid cake 106. In one embodiment of the invention, a portion can mean any part up to and including the whole. In another embodiment of the invention a portion can mean at least 5% by weight of the solvent is removed. In another embodiment of the invention a portion can mean at least 10% by weight of the solvent is removed. In another embodiment of the invention a portion can mean at least 25% by weight of the solvent is removed. In another embodiment of the invention a portion can mean at least 50% by weight of the solvent is removed. In another embodiment of the invention, a portion can mean at least 75% by weight of the solvent is removed. In another embodiment of the invention a portion can mean at least 85% by weight of the solvent is removed. In another embodiment of the invention a portion can mean at least 90% by weight of the solvent is removed. The water-wet carboxylic acid cake 106, is preferably in the range of about 0.5-30% moisture, more preferably in the range of 1-20% moisture, and most preferably in the range of 1-5% moisture. The residual moisture of the water-wet carboxylic acid cake 106, should contain less than about 2% solvent on a mass basis. Additionally, the water-wet carboxylic acid cake should contain less than 1% of any metals (e.g. cobalt, manganese, etc. . . . ), typically used as catalysts in p-xylene oxidation, in the slurry mixture in conduit 101, should remain in the water-wet carboxylic acid cake 106.

Wash water is introduced into the second solid-liquid separation device 120 via conduit 104. The wash water should be, on a continuous basis, comprise a mass feed rate in ratio with the solids in 103 in the range of about 0.1:1 to 1.5:1, preferably in the range of 0.1:1 to 0.6:1, most preferably in the range of 0.2:1 to 0.4:1. There are no limitations on the temperature or pressure of the wash water including the use of vaporized water, steam, or a combination of water and steam, as wash.

The second solid-liquid separation device 120 can typically be comprised of, but not limited to, the following types of devices: centrifuges, cyclones, rotary drum filters, belt filters, press filters, etc. The second solid-liquid separation device 120 can operate within a temperature range of from approximately 40° C. to 155° C. Preferably, the second solid-liquid separation device 120 can operate within a temperature range of from approximately 80° C. to 150° C. Most preferably, the second solid-liquid separation device 120 can operate within a temperature range of from about 90° C. to 150° C.

Optionally, the solvent/water byproduct liquor from the second solid-liquid separation device 105, is segregated from the solvent mother liquor stream produce by the first solid-liquid separation device 102.

Step (3) comprises adding a diol 107 to the water-wet carboxylic acid cake 106 in a carboxylic acid/diol mixing zone 130 to remove a portion from the water-wet carboxylic acid cake 106 of the water to form the carboxylic acid/diol mixture 108.

Finally, the water-wet carboxylic acid cake 106, which is now substantially free of solvent is combined with a diol 107 in a carboxylic acid mixing zone 130, to form a carboxylic acid/diol mixture 108 suitable for PET production and other polyesters in device 130. Conduit 109 is used to remove the portion of water from the water-wet carboxylic acid cake 106. In one embodiment of the invention, a portion can mean any part up to and including the whole. In another embodiment of the invention a portion can mean at least 5% by weight of the water is removed. In another embodiment of the invention a portion can mean at least 10% by weight of the water is removed. In another embodiment of the invention a portion can mean at least 25% by weight of the water is removed. In another embodiment of the invention a portion can mean at least 50% by weight of the water is removed. In another embodiment of the invention, a portion can mean at least 75% by weight of the water is removed. In another embodiment of the invention a portion can mean at least 85% by weight of the water is removed. In another embodiment of the invention a portion can mean at least 90% by weight of the water is removed.

There are no special limitations on the device 130 with the exception that it must provide intimate contact between the water-wet carboxylic acid cake 106, and the diol 107 to produce a the carboxylic acid/diol mixture 108. Examples of such devices include, but are not limited to the following: an agitated vessel, static mixer, screw conveyor, PET esterification reactor(s), etc. (Note: a solid eductor could be used to introduce the water-wet carboxylic acid cake into device 130). Nor is there any specific limitation on the temperature range at which device 130 can operate. However, it is preferable that the temperature of device 130 does not exceed approximately 280° C., temperatures normally found within PET esterification reactors.

The diol in conduit 107 is introduced in such a manner as to displace the water as the dominant slurrying liquid. This can be accomplished by introducing a diol via conduit 107 as a saturated liquid at a temperature which is sufficient to vaporized the water. Preferably, the diol in conduit 107 is introduced as a saturated or superheated vapor. The diol in conduit 107 is selected from the group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 107 is ethylene glycol. Note that within the system shown in FIG. 1, a substantially dry carboxylic acid solid is not formed. In one embodiment of the invention substantially dry generally means less than 5% by weight moisture. In another embodiment of the invention, another range can be less than 10% by weight moisture. In another embodiment of the invention, still another range can be less than 15% by weight moisture. In another embodiment of the invention, yet another range for substantially dry can mean less than 20% by weight moisture. In another embodiment of the invention, another range for substantially dry can mean less than 25% by weight moisture. In yet another embodiment of the invention the substantially dry would be the moisture content obtained through the use of mostly mechanical means for drying and wherein the majority of the drying is not accomplished through evaporation. Majority as used herein means greater than 50%. The primary economic advantage in not forming a carboxylic acid dry solid is the elimination of solids handling equipment (e.g. convey systems, silos, etc. . . . ).

In a third embodiment of this invention show in FIG. 1, a process for producing a carboxylic acid/diol mixture 108, the process comprising the following steps.

Step (1) comprises removing a solvent from a carboxylic acid/solvent slurry 101 in a solid-liquid separation zone 140; wherein a portion of the solvent in the carboxylic acid/solvent slurry 101 is replaced with water to form a water-wet carboxylic acid cake 106.

In Step (1) the second solid-liquid separation device 120 and the first solid-liquid separation device 110 in the second embodiment of this invention can be combined to form a single device capable of performing both solid-liquid separations. This is shown schematically in FIG. 1 showing a solid-liquid displacement zone 140 by a dashed outline box around devices 110 and 120. The removal of the solvent from a carboxylic/solvent slurry 101 in a solid-liquid separation zone 140 to form a water-wet carboxylic acid cake can be accomplished by any means know in the art. The solid-liquid separation zone 140 comprises any device capable of performing both operations of the first solid-liquid separation device 110 and the second solid-liquid separation device 120 described in the second embodiment of this invention. The device in the solid-liquid separation zone 140 can typically be comprises of but not limited to, the following type of devices centrifuges, cyclones, filters, and such or combination thereof.

Step (2) comprises adding a diol 107 to the water-wet carboxylic acid cake 106 in a carboxylic acid/diol mixing zone 130 to remove a portion of the water to form the carboxylic acid/diol mixture 108.

Step (2) is identical to step (3) described in the second embodiment of this invention.

In a fourth embodiment of this invention is provided in FIG. 2, comprises a process for producing a terephthalic acid/diol mixture 208 is provided, the process comprises adding a diol 207 to a water-wet terephthalic acid cake 206 in a terephthalic acid/diol mixing zone 230 to remove a portion of the water to form the terephthalic acid/diol mixture 208.

The terephthalic acid/diol mixing zone 230, the diol 207, the terephthalic acid/diol mixture 208 and the water-wet terephthalic acid cake 206 are described subsequently in a fifth embodiment of this invention.

In the fifth embodiment of this invention shown in FIG. 2, a process for producing a terephthalic acid/diol mixture 208 is provided. The process comprising the following steps.

Step (1) comprises removing in a first solid-liquid separation device 210 impurities from a terephthalic acid/solvent slurry 201 to form a terephthalic acid cake with solvent 203 and a TPA solvent mother liquor stream 202.

Conduit 201 contains a terephthalic acid/solvent slurry comprising a terephthalic acid, impurities and a solvent. The impurities comprises residual catalyst (typically but not limited to cobalt, manganese, or bromine). Suitable solvents include, but are not limited to, aliphatic mono-carboxylic acids, preferably containing 2 to 6 carbon atoms, or benzoic acid and mixtures thereof and mixtures of these compounds with water. Preferably, the solvent is comprised of mainly acetic acid and/or some water. The ratio of acetic acid to water can range from 50:50 to 99:1 acetic acid to water by mass, more preferably in the range of 85:15 to 95:5, and most preferably in the range of 90:10 to 95:5. The terephthalic acid/solvent slurry 201 is in the range of about 10-40% by weight terephthalic acid. Preferably the terephthalic acid/solvent slurry 201 is in the range of 25-35% by weight terephthalic acid. Most preferably, the terephthalic acid/solvent slurry 201 is in the range of 30-35% by weight terephthalic acid. The terephthalic acid/solvent slurry in conduit 201 is then introduced into a first solid-liquid separation device 210, wherein a portion of the solvent mother liquor is recovered in conduit 202. The solvent mother liquor 202 comprises a portion of the solvent.

The first solid-liquid separation device 210 is any device capable of efficiently separating solids and liquids. The first solid-liquid separation device 210 can typically be comprised of, but not limited to, the following types of devices: centrifuges, cyclones, rotary drum filters, belt filters, press filters, etc. The first solid-liquid separation device 210 can operate within a temperature range of from about 40° C. to 155° C. Preferably the first solid-liquid device 210 can operate within a temperature range of from approximately 80° C. to 150° C. Most preferably the first solid-liquid separation device 210 can operate within a temperature range of from about 90° C. to 150° C. A terephthalic acid cake with solvent 203, is produced wherein the moisture composition of the terephthalic acid cake with solvent is in the range of 0.5-30% moisture, preferably in the range of 1-10% moisture, most preferably in the range of 1-5% moisture. Optionally, the residual solvent can be removed by a gas displacement step to minimize solvent contamination with wash.

Step (2) comprises removing a portion of a solvent in a second solid-liquid separation device 220 from the terephthalic acid cake with solvent 203 to form a water-wet terephthalic acid cake 206 and a TPA solvent/water byproduct liquor 205.

The terephthalic acid cake with solvent 203, is then subjected to a wash or "rinsing" with water in the second solid-liquid separation device, 220, wherein a portion of the initial solvent is replaced with water to form a water-wet terephthalic acid cake 206. The water-wet terephthalic acid cake 206, is preferably in the range of 0.5-30% moisture, more preferably in the range of about 1-20% moisture, and most preferably in the range of 1-5% moisture. The residual moisture of the water-wet terephthalic acid cake 206, should contain less than about 2% solvent on a mass basis. Additionally, the water-wet terephthalic acid cake should contain less than 1% of any metals (e.g. cobalt, manganese, etc. . . . ), typically used as catalysts in p-xylene oxidation, in the slurry mixture in conduit 201, should remain in the water-wet terephthalic acid cake 206.

Wash water is introduced into device 220 via conduit 204. The wash water should be, on a continuous basis, comprise a mass feed rate in ratio with the solids in 203 in the range of about 0.1:1 to 1.5:1, preferably in the range of 0.1:1 to 0.6:1, most preferably in the range of 0.2:1 to 0.4:1. There are no limitations on the temperature or pressure of the wash water including the use of vaporized water, steam, or a combination of water and steam as wash.

The second solid-liquid separation device 220 can typically be comprised of, but not limited to, the following types of devices: centrifuges, cyclones, rotary drum filters, belt filters, press filters, etc. The second solid-liquid separation device 220 can operate within a temperature range of from about 40° C. to 155° C. Preferably, the second solid-liquid separation device 220 can operate within a temperature range of from about 80° C. to 150° C. Most preferably, the second solid-liquid separation device 220 can operate within a temperature range of from about 90° C. to 150° C.

Optionally, the solvent/water byproduct liquor from the second solid-liquid separation device 205, is segregated from the solvent mother liquor stream produce by the first solid-liquid separation device 202.

Step (3) comprises adding a diol 207 to the water-wet terephthalic acid cake 206 in a terephthalic acid/diol mixing zone 230 to remove a portion from the water-wet terephthalic acid cake 206 of the water to form the terephthalic acid/diol mixture 208.

Finally, the water-wet terephthalic acid cake 206, which is now substantially free of solvent is combined with a diol 207, to form a terephthalic acid/diol mixture suitable for PET production and other polyesters in device 230. Conduit 209 is used to remove the portion of water from the water-wet carboxylic acid cake 206. There are no special limitations on the device 230 with the exception that it must provide intimate contact between the water-wet terephthalic acid cake 206, and the diol 207 to produce a the terephthalic acid/diol mixture 208. Examples of such devices include, but are not limited to the following: an agitated vessel, static mixer, screw conveyor, PET esterification reactor(s), etc. . . . (Note: a solid eductor could be used to introduce the water-wet terephthalic acid cake into device 230). Nor is there any specific limitation on the temperature range at which device 230 can operate. However, it is preferable that the temperature of device 230 does not exceed approximately 280° C., temperatures normally found within PET esterification reactors.

The diol in conduit 207 is introduced in such a manner as to displace the water as the dominant slurrying liquid. This can be accomplished by introducing a diol via conduit 207 as a saturated liquid at a temperature which is sufficient to vaporized the water. Preferably, the diol in conduit 207 is introduced as a saturated or superheated vapor. The diol in conduit 207 is selected from the group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 207 is ethylene glycol. Note that within the system shown in FIG. 1, a substantially dry terephthalic acid solid is not formed. The primary economic advantage in not forming a terephthalic acid dry solid is the elimination of solids handling equipment (e.g. convey systems, silos, etc. . . . ).

In a sixth embodiment of this invention show in FIG. 2, a process for producing a terephthalic acid/diol mixture 208 is provided. The process comprising the following steps:

Step (1) removing a solvent from a terephthalic acid/solvent slurry 201 in a solid-liquid separation zone 240; wherein a portion of the solvent in the terephthalic acid/solvent slurry 201 is replaced with water to form a water-wet terephthalic acid cake 206.

In Step (1) the second solid-liquid separation device 220 and the first solid-liquid separation device 210 in the second embodiment of this invention can be combined to form a single device capable of performing both solid-liquid separations. This is shown schematically in FIG. 2 showing a solid-liquid displacement zone 240 by a dashed outline box around devices 210 and 220. The removal of the solvent from a carboxylic/solvent slurry 201 in a solid-liquid separation zone 240 to form a water-wet terephthalic acid cake can be accomplished by any means know in the art. The solid-liquid separation zone 240 comprises any device capable of performing both operations of the first solid-liquid separation device 210 and the second solid-liquid separation device 220 described in the second embodiment of this invention. The device in the solid-liquid separation zone 240 can typically be comprises of but not limited to, the following type of devices centrifuges, cyclones, filters, and such or combination thereof.

Step (2) comprises adding a diol 207 to the water-wet terephthalic acid cake 206 in a terephthalic acid/diol mixing zone 230 to remove a portion of the water to form the terephthalic acid/diol mixture 208.

Step (2) is identical to Step (3) described in the fifth embodiment of this invention.

We claim:

1. A process for producing a carboxylic acid/diol mixture suitable for the production of polyesters, said process comprising adding a diol to a water-wet carboxylic acid cake in a carboxylic acid/diol mixing zone to remove at least a portion of the water from said water-wet carboxylic acid cake to form said carboxylic acid/diol mixture; wherein said carboxylic acid/diol mixture is produced without the isolation of a substantially dry carboxylic acid solid; wherein said water is displaced from said water-wet carboxylic acid cake by the addition of said diol.

2. A process according to claim 1 wherein said carboxylic acid is selected from a group consisting of terephthalic acid, isophthalic acid, naphthalene dicarboxylic acid, trimellitic acid, and mixtures thereof.

3. A process according to claim 1 or 2 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

4. A process according to claim 1 wherein said carboxylic acid/diol mixing zone comprises at least one device selected from the group consisting of an agitated vessel, a static mixer, and a screw conveyor.

5. A process for producing a carboxylic acid/diol mixture suitable for the production of polyesters, said process comprising the following steps:
   (a) removing in a first solid-liquid separation device impurities from a carboxylic acid/solvent slurry to form a carboxylic acid cake with acetic acid and a solvent mother liquor stream;
   (b) removing a portion of a solvent in a second solid-liquid separation device from said carboxylic acid cake with acetic acid to form a water-wet carboxylic acid cake and a solvent/water byproduct liquor;
   (c) adding a diol to said water-wet carboxylic acid cake in a carboxylic acid/diol mixing zone to remove at least a portion of the water from said water-wet carboxylic acid cake to form said carboxylic acid/diol mixture; wherein said carboxylic acid/diol mixture is produced without the isolation of a substantially dry carboxylic acid solid; wherein said water is displaced from said water-wet carboxylic acid cake by the addition of said diol.

6. A process according to claim 5 wherein said carboxylic acid is selected from a group consisting of terephthalic acid, isophthalic acid, naphthalene dicarboxylic acid, trimellitic acid and mixtures thereof.

7. A process according to claim 5 or 6 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

8. A process according to claim 5 wherein said diol/carboxylic acid mixing zone comprises at least one device selected from the group consisting of an agitated vessel, a static mixer, and a screw conveyor.

9. A process for producing a carboxylic acid/diol mixture suitable for the production of polyesters, said process comprising the following steps:
   (a) removing a solvent from a carboxylic acid/solvent slurry in a solid-liquid separation zone; wherein a portion of the solvent in said carboxylic acid/solvent slurry is replaced with water to form a water-wet carboxylic acid cake;
   (b) adding a diol to said water-wet carboxylic acid cake in a carboxylic acid/diol mixing zone to remove at least a portion of the water from said water-wet carboxylic acid cake to form said carboxylic acid/diol mixture; wherein said carboxylic acid/diol mixture is produced without the isolation of a substantially dry carboxylic acid solid; wherein said water is displaced from said water-wet carboxylic acid cake by the addition of said diol.

10. A process according to claim 9 wherein said carboxylic acid is selected from a group consisting of terephthalic acid, isophthalic acid, naphthalene dicarboxylic acid, trimellitic and mixtures thereof.

11. A process according to claim 9 or 10 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

12. A process according to claim 9 wherein said carboxylic acid/diol mixing zone comprises at least one device selected from the group consisting of an agitated vessel, a static mixer, and a screw conveyor.

13. A process for producing a terephthalic acid/diol mixture, said process comprising adding a diol to a water-wet terephthalic acid cake in a terephthalic acid/diol mixing zone to remove a portion of the water to form said terephthalic acid/diol mixture.

14. A process according to claim 13 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

15. A process according to claim 13 wherein said diol is ethylene glycol.

16. A process according to claim 13, 14 or 15 wherein said adding occurs at a temperature between about 40° C. and about 290° C.

17. A process according to claim 13 wherein said terephthalic acid/diol mixing zone comprises a device selected from the group consisting of an agitated vessel, a static mixer, a screw conveyor, and a PET esterification reactor.

18. A process for producing a terephthalic acid/diol mixture suitable for the production of polyesters, said process comprising the following steps:
   (a) removing in a first solid-liquid separation device impurities from a terephthalic acid/solvent slurry to form a terephthalic acid cake with acetic acid;
   (b) removing a portion of a solvent in a second solid-liquid separation device from said terephthalic acid cake with acetic acid to form a water-wet terephthalic acid cake; and
   (c) adding a diol to said water-wet terephthalic acid cake in a terephthalic acid/diol mixing zone to remove at least a portion of the water from said water-wet carboxylic acid cake to form said terephthalic acid/diol mixture; wherein said carboxylic acid/diol mixture is produced without the isolation of a substantially dry carboxylic acid solid; wherein said water is displaced from said water-wet carboxylic acid cake by the addition of said diol.

19. A process according to claim 18 wherein said first solid-liquid separation device is operated at a temperature between about 40° C. to about 155° C.

20. A process according to claim 19 wherein said second solid-liquid separation device is operated at a temperature between about 40° C. to about 155° C.

21. A process according to claim 18 or 20 wherein said adding occurs at a temperature between about 40° C. and about 290° C.

22. A process according to claim 18 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

23. A process according to claim 18 wherein said diol is ethylene glycol.

24. A process according to claim 18 wherein said terephthalic acid/diol mixing zone comprises a device selected from the group consisting of an agitated vessel, a static mixer, and a screw conveyor.

25. A process for producing a terephthalic acid/diol mixture suitable for the production of polyesters, said process comprising the following steps:
  (a) removing a solvent from a terephthalic acid/solvent slurry in a solid-liquid separation zone; wherein a portion of the solvent in said terephthalic acid/solvent slurry is replaced with water to form a water-wet terephthalic acid cake;
  (b) adding a diol to said water-wet terephthalic acid cake in a terephthalic acid/diol mixing zone to remove at a portion the water from said water-wet carboxylic acid cake to form said terephthalic acid/diol mixture; wherein said carboxylic acid/diol mixture is produced without the isolation of a substantially dry carboxylic acid solid; wherein said water is displaced from said water-wet carboxylic acid cake by the addition of said diol.

26. A process according to claim 25 wherein said solid-liquid displacement zone is operated at a temperature between about 40° C. to about 155° C.

27. A process according to claim 25 wherein said adding occurs at a temperature between about 40° C. and 290° C.

28. A process according to claim 25 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

29. A process according to claim 25 wherein said diol is ethylene glycol.

30. A process according to claim 25 wherein said diol/terephthalic acid mixing zone comprises a device selected from the group consisting of an agitated vessel, a static mixer, and a screw conveyor.

* * * * *

UNITED STATES PATENT AND TRADEMARK OFFICE
CERTIFICATE OF CORRECTION

PATENT NO. : 7,226,986 B2 Page 1 of 1
APPLICATION NO. : 11/077481
DATED : June 5, 2007
INVENTOR(S) : Lin et al.

It is certified that error appears in the above-identified patent and that said Letters Patent is hereby corrected as shown below:

Column 14, Line 2, Claim 25 "at a" should read --at least a--;
Column 14, Line 3, Claim 25 "portion the" should read --portion of the--.

Signed and Sealed this

Seventh Day of July, 2009

JOHN DOLL
*Acting Director of the United States Patent and Trademark Office*